(12) United States Patent
Navarrini et al.

(10) Patent No.: US 7,141,704 B2
(45) Date of Patent: Nov. 28, 2006

(54) PROCESS FOR PREPARING HYDROFLUOROETHERS

(75) Inventors: Walter Navarrini, Milan (IT); Marco Galimberti, Milan (IT); Giovanni Fontana, Verona (IT)

(73) Assignee: Solvay Solexis S.P.A., Milan (IT)

( * ) Notice: Subject to any disclaimer, the term of this patent is extended or adjusted under 35 U.S.C. 154(b) by 285 days.

(21) Appl. No.: 10/809,868

(22) Filed: Mar. 26, 2004

(65) Prior Publication Data

US 2004/0192974 A1   Sep. 30, 2004

(30) Foreign Application Priority Data

Mar. 27, 2003 (IT) .......................... MI2003A0606

(51) Int. Cl.
*C07C 41/01* (2006.01)
(52) U.S. Cl. ................ 568/615; 568/616; 568/677; 568/683; 562/849; 562/856
(58) Field of Classification Search ................ 568/615, 568/616, 677, 683; 562/849, 856
See application file for complete search history.

(56) References Cited

U.S. PATENT DOCUMENTS

| | | | |
|---|---|---|---|
| 3,113,967 A | 12/1963 | Fawcett | 562/849 |
| 3,114,778 A | 12/1963 | Fritz et al. | 568/674 |
| 3,250,808 A | 5/1966 | Moore, Jr. et al. | 562/586 |
| 3,351,644 A | 11/1967 | Hauptschein et al. | 562/857 |
| 3,847,978 A | 11/1974 | Sianesi et al. | 562/577 |
| 3,962,460 A | 6/1976 | Croix et al. | 424/342 |
| 5,488,142 A | 1/1996 | Fall et al. | 560/227 |
| 5,750,797 A | 5/1998 | Vitcak et al. | 568/683 |
| 6,013,795 A | 1/2000 | Manzara et al. | 544/106 |
| 6,127,498 A | 10/2000 | Tonelli et al. | 526/247 |

FOREIGN PATENT DOCUMENTS

| | | |
|---|---|---|
| EP | 1 375 469 A1 | 1/2004 |
| GB | 1 216 639 | 5/1969 |
| IT | MI2002A 001365 | 12/2003 |
| IT | MI2003A 000018 | 7/2004 |
| IT | MI2003A 000019 | 7/2004 |
| WO | WO 97/38962 | 10/1997 |
| WO | WO 99/37598 | 7/1999 |
| WO | WO 99/47480 | 9/1999 |

*Primary Examiner*—Rosalynd Keys
(74) *Attorney, Agent, or Firm*—Arent Fox PLLC

(57) ABSTRACT

Process for obtaining hydrofluoroethers of formula (I):

$$A\text{-}(R_f)_{n0}\text{---}CF(R_{f1})\text{---}O\text{---}R_h \qquad (I)$$

wherein a mono- or bifunctional carbonyl compound of formula (IV):

$$B\text{---}R_f\text{---}C(O)R_{f1} \qquad (IV)$$

is reacted with at least one equivalent of a fluoroformate of formula (III)

$$R\text{---}OC(O)F \qquad (III)$$

in the presence of an ion fluoride compound (catalyst) and of a dipolar aprotic organic compound, liquid and inert under the reaction conditions.

26 Claims, No Drawings

PROCESS FOR PREPARING HYDROFLUOROETHERS

The present invention relates to a catalytic process for preparing hydrofluoroethers (HFE) in high yields and selectivity.

More specifically the present invention relates to hydrofluoroethers having one end group of the —O—$R_h$ type wherein $R_h$ is a saturated or unsaturated hydrocarbon group.

Processes to obtain hydrofluoroethers are known in the prior art.

U.S. Pat. No. 3,962,460 describes hydrofluoroethers and their synthesis. For example the $CF_3$—$CF(CF_3)$—$OCH_2Cl$, $CF_3$—$CF(CF_3)$—$OCH_3$ compounds described in the patent are prepared by reaction of dimethylsulphate, potassium fluoride and a carbonyl reactant in a large excess. The process has the drawback that the metal fluoride is used as a reactant, and significant amounts of reactants and inorganic salts, formed during the reaction, remain in the final mixture. These salts, must be disposed, as for example potassium sulphate. Moreover the yields of this process are not high.

Patent application WO 97/38962 describes a process for preparing HFE in dipolar aprotic solvents by the following reactants: a) a (per)fluorocarbonyl compound; b) fluorides, generally anhydrous metalfluorides; in particular KF; c) tertiary or aromatic amines in amounts to neutralize the acid contaminants present in the reaction mixture, mainly HF; d) optionally a phase transfer catalyst. The so prepared mixture is then added to an alkylating agent, for example methyl sulphate, obtaining hydrofluoroethers. This process has the drawback that metal fluoride amounts equal to at least the stoichiometric value, are used, with respect to the acylfluorides to be alkylated. Further the yields are high only when tertiary or aromatic amines, in the presence of an excess of alkylating agent, are used. Besides, as said for the previous patent, the mixture at the end of the reaction contains significant amounts of reactants and inorganic salts to be disposed.

Patent application WO 99/37598 describes a process for preparing hydrofluoroethers by reaction of a fluoroalkoxide and an alkyl fluorovinylether in a dipolar aprotic solvent. The drawback of this process is that the two reactants must be prepared. The fluoroalkoxide is obtained in anhydrous environment by reaction of an acylfluoride with an excess of anhydrous metal fluorides, for example KF. The alkyl fluorovinylether compound is obtained in two steps, by reaction of an alcohol with a fluoroolefin and then dehydrofluorination of the obtained compound. The formation process of the fluoroalkoxide has the drawback to use a high amount of a anhydrous metalfluoride per mole of acylfluoride alkylate. The formation process of the alkyl fluorovinylether has furthermore the drawback to use fluoroolefins, compounds not always available and often toxic.

Patent application WO 99/47480 describes a process for preparing hydrofluoroethers, wherein a perfluorocarbonyl compound is reacted with an alkylating agent $R^I$—F in the presence of an acid Lewis catalyst, for example $SbF_5$. The drawback of this process is that the catalysts can be easily deactivated by impurities of the starting products and by reaction by-products, for example ethylene when $R^I$—F is $CH_3CH_2$—F, or also by $H_2O$ traces of polluting basic compounds. Furthermore the mono-fluoroalkyl alkylating agent must be prepared. The alkylation reaction between the carbonyl fluorinated product and the $R^I$—F alkylating agent in the presence of the acid catalyst is an exothermal equilibrium reaction. The yields are good only by using a strong excess of alkylating agent $R^I$—F with respect to the carbonyl compound. Besides, the separation phase of the raw reaction product from the catalyst can be difficult since, as said, the reaction is anequilibrium reaction and therefore the catalyst promotes also the reverse retrocondensation reaction. According to the Examples of this patent application the yields in hydrofluoroethers, starting from a perfluoro carbonyl compound and an alkylating agent, are high only when $CH_3F$ is used as alkylating agent.

The need was felt to have available a process for preparing hydrofluoroethers having one —O—$R_h$ end group, wherein $R_h$ is a saturated or unsaturated hydrocarbon group, having the following feature combination:
high condensation yields, even when $R_h$ contains one or more carbon atoms;
possibility of recycle of the catalyst;
separation of the hydrofluoroether condensation products by simple techniques;
low environmental impact of the by-products to be disposed.

The Applicant has surprisingly and unexpectedly found a process of preparation of hydrofluoroether compounds solving the above technical problem.

An object of the present invention is a process for obtaining hydrofluoroethers of formula:

wherein:
n0 is zero or 1;
$R_f$ is a bivalent radical:
$C_1$–$C_{20}$, preferably $C_2$–$C_{12}$, linear or branched (per)fluoroalkylene, optionally containing one or more oxygen atoms; or
—$CFW'O$—$(R_{f2})$—$CFW$—, wherein W and W', equal or different, are F, $CF_3$; $R_{f2}$ is a (per)fluoropolyoxyalkylene containing one or more of the following units, statistically distributed along the chain, $(C_3F_6O)$; —(CFWO) wherein W is as above; $(C_2F_4O)$, $(CF_2(CF_2)_zCF_2)$ wherein z is an integer equal to 1 or 2; $(CH_2CF_2CF_2)$;
$R_{f1}$ is F or a $C_1$–$C_{10}$ linear or branched (per)fluoroalkyl or (per)fluorooxyalkyl radical;
$R_h$ is a $C_1$–$C_{20}$, preferably $C_1$–$C_{10}$, linear, branched when possible, saturated or unsaturated when possible alkyl; or $R_h$ is $C_1$–$C_{20}$ alkylaryl, optionally containing heteroatoms selected from F, O, N, S, P, Cl; and/or functional groups preferably selected from —$SO_2F$, —$CH$=$CH_2$, —$CH_2CH$=$CH_2$ and $NO_2$;
A=F, $(R_{h2}O)$—$CF(R_{f4})$—, —$C(O)F$, wherein
$R_{h2}$, equal to or different from $R_h$, has the $R_h$ meanings;
$R_{f4}$, equal to or different from $R_{f1}$, has the $R_{f1}$ meanings;

wherein a mono- or bifunctional carbonyl compound of formula:

wherein B is F or —$C(O)R_{f4}$, $R_f$, $R_{f1}$ and $R_{f4}$ being as above, is reacted with at least one equivalent of a fluoroformate of formula:

wherein R=$R_h$ or $R_{h2}$ as above;

in the presence of an ion fluoride compound which acts as a catalyst and of a dipolar aprotic organic liquid compound, inert in the reaction conditions.

The $(C_3F_6O)$ unit of $R_{f2}$ in $R_f$ can be $(CF_2CF(CF_3)O)$ or $(CF(CF_3)CF_2O)$.

The reaction between the carbonyl compound (IV) and the fluoroformate (III) develops one $CO_2$ mole for equivalent of $-C(O)R_{f1}$ or $-C(O)R_{f4}$.

When the compound (IV) is bifunctional, i.e. $B=-C(O)R_{f4}$, it is possible to react the carbonyl compound with two fluoroformate (III) having a different R.

Preferably in formula (I) $R_{f1}$ and $R_{f4}$ in A, independently the one from the other, are F, $CF_3$.

Preferably when $R_f$ is a (per)fluoroalkylene it is selected from the following groups: $-CF_2-$, $-CF_2CF_2-$, $-CF_2CF_2CF_2-$, $-CF_2(CF_3)CF-$; when $R_f$ contains one oxygen atom it preferably has the $-CF_2CF(OCF_3)-$ meaning.

$R_{f2}$ is a perfluoropolyoxyalkylene chain having number average molecular weight from 66 to 12,000, preferably from 100 to 5,000, more preferably from 300 to 2,000.

Preferably the perfluorooxyalkylene chain of $R_{f2}$ is selected from the following structures:
a) $-(CF_2CF_2O)_m(CF_2O)_n(CF_2CF(CF_3)O)_p(CF(CF_3)O)_q-$;
b) $-(CF_2O)_n(CF_2CF(CF_3)O)_p(CF(CF_3)O)_q-$;
c) $-(CF_2CF_2O)_m(CF_2O)_n$;
wherein:
m is comprised between 0 and 100 extremes included;
n is comprised between 0 and 50 extremes included;
p is comprised between 0 and 100 extremes included;
q is comprised between 0 and 60 extremes included;
m+n+p+q>0 and the number average molecular weight of $R_p$ being in the above limits.

The perfluorooxyalkylene c) is preferred, wherein the m/n ratio ranges from 0.1 to 10, n being differnt from zero and the number average molecular weight within the above limits.

Preferably $R_h$ and $R_{h2}$ have the following meanings:

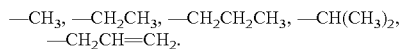

The ion fluoride compound is any compound capable to generate ion fluorides when in the presence of dipolar aprotic solvents, at temperatures from 20° C. up to 200° C.

Examples of dipolar aprotic solvents are acetonitrile, dimethylformamide, glyme, ethylene polyoxides dimethylethers (PEO-dimethylethers); preferably tetraglyme and PEO-dimethylethers having a number average molecular weight in the range 134–2,000 are used.

The ion fluoride compound is preferably selected from metal fluorides, in particular alkaline or alkaline-earth metal fluorides; AgF; alkylammoniumfluorides, alkylphosphoniumfluorides, wherein the nitrogen or respecively the phosphor atom can be substituted with one or more $C_1-C_8$ alkyl groups, equal to or different from each other.

CsF and KF are the preferred catalysts.

Optionally the catalyst is supported, for example on a porous material, such as for example $Al_2O_3$ or MgO.

The catalyst amounts, expressed in % by moles, are in the range 0.1%–50% with respect to the mono- or bifunctional carbonyl compound of formula (IV).

As said, the reaction between the carbonyl compound (IV) and fluoroformate (III) takes place in the presence of a dipolar aprotic organic compound, liquid and inert in the reaction conditions. Said organic compound is for example acetonitrile, dimethylformamide, glyme, ethylene polyoxides dimethylethers (PEO-dimethylethers); preferably tetraglyme and PEO-dimethylethers having number average molecular weight in the range 134–2,000 are used.

The ratio by weight betwen the dipolar aprotic organic compound and the ion fluoride compound can range from 1:100 to 100:1.

Optionally in the process according to the present invetion tertiary amines and/or phase transfer catalysts can be used. It has been found that these compounds facilitate the condensation reaction between (III) and (IV).

The reaction temperature in the process acording to the present invention is from 60° C. to 200° C. preferably from 80° C. to 150° C.

The pressure at which one oeprates can be the atmospheric pressure or higher, even up to 30 atm.

The formation of the reaction products can for example be followed by monitoring in the time the pressure increase ($CO_2$ formation), until the pressure remains constant.

The reaction time is from 1 h to 100 h, preferably from 6 h to 72 h.

When the carbonyl compound (IV) is bifunctional, the reaction can also take place in two steps. In the first step one fluoroformate mole (III) ($R=R_h$) is added for the first equivalent of carbonyl compound (IV). At the end of the reaction one mole of a different fluoroformate ($R=R_{h2}$) is added, to react the second equivalent of the carbonyl compound (IV). Alternatively the two fluoroformates can be contemporaneously added.

The yields are calculated as percent ratio between the obtained HFE moles and the initial moles of the carbonyl compound (IV).

The process according to the present invention allows to obtain high HFE yields, generally higher than 70%.

Furthermore the selectivity, defined as percent ratio by moles between the HFE and the reacted carbonyl compound (IV), is generally higher than 90%.

At the end of the reaction the condensation products can be separated from the raw reaction product by distillation or by decantation. The skilled in the art, depending on the boiling points of the final products and the dipolar aprotic compound to be used, can select the most suitable method.

It is thus possible to recover and reuse, even more times, the suspension/solution of the ion fluoride compound in the dipolar aprotic organic compound. One can operate to maintain the suspension/solution of the catalyst in the condensation reactor: in this case the reactants are fed into the reactor and only the condensation products, optionally the unreacted compounds, are discharged.

The process according to the present invention can be carried out in a discontinuous or in a continuous way.

The carbonyl compounds (IV) can be prepared according to the disclosures of the following patents: U.S. Pat. No. 3,113,967, U.S. Pat. No. 3,114,778, U.S. Pat. No. 3,250,808, U.S. Pat. No. 3,351,644, U.S. Pat. No. 6,013,795, U.S. Pat. No. 3,847,978, U.S. Pat. No. 6,127,498, U.S. Pat. No. 5,488,142, the patent applications in Italy Nos. MI 2003A 000018, MI 2003A 000019 and MI 2002A 001365.

The fluoroformate compounds (III) are known in the art and can be prepared according to the disclosures of the patent GB 1,216,639.

The compounds prepared according to the present invention are used as refrigerants, foaming agents, solvents, lubricants, heat transfer and have a reduced environmental impact.

The following Examples illustrate with non limitative purposes the present invention.

EXAMPLE 1

 Synthesis 0.36 g of CsF in powder (2.4 mmoles) and 2.02 g of tetraglyme ($CH_3O(CH_2CH_2O)_4CH_3$) are introduced by dry-box in a 25 ml autoclave equipped with pressure transducer and magnetic anchor. After having removed the uncondensable products by a vacuum system, 23 mmoles of acylfluoride $(CF_3O)$ $(CF_3)CFCOF$ and then 23 mmoles of methylfluoroformate $(CH_3OC(O)F)$ are condensed in the autoclave. The autoclave is put in an oil bath maintained at the tmeperature of 100° C. After 36 hours the heating is turned out and the autoclave content is transferred into a vacuum system. By a trap-to-trap distillation with traps maintained at the temperatures of respectively −110° C. and −196° C., 5.25 g of distillate are isolated in the trap at −110° C., which analyzed by GC, results to contain 84% by weight of the product $(CF_3O)$ $(CF_3)CFCF_2OCH_3$. The alkylation yield as ratio between the obtained HFE moles and the moles of the used carbonyl compound is 72%. The alkylation yield with respect to the converted acyl fluoride (selectivity) is 95%.

EXAMPLE 2

$(CF_3O)$ $(CF_3)CFCF_2OCH_2CH_3$ Synthesis

One proceeds as in the Example 1 but by feeding 15 mmoles of the same acyl-fluoride and 15 mmoles of ethylfluoroformate $(CH_3CH_2OC(O)F)$. After trap-to-trap distillation 3.21 g of distillate are isolated containing 87% by weight of the desired product with an alkylation yield with respect to the initial acylfluoride of 76%. The selectivity is 96%.

EXAMPLE 3

$(CF_3O)$ $(CF_3)CFCF_2OCH_2CH=CH_2$ Synthesis

One proceeds as in the Example 1 but by feeding 15 mmoles of the same acyl-fluoride and 15 mmoles of allylfluoroformate $(CH_2=CHCH_2OC(O)F)$. After trap-to-trap distillation 3.76 g of distillate are isolated containing 95% by weight of the desired product with an alkylation yield with respect to the initial acylfluoride of 81%. The selectivity is 97%.

EXAMPLE 4

$(CF_3O)$ $(CF_3)CFCF_2OCH(CH_3)_2$ Synthesis

One proceeds as in the Example 1 but by feeding 15 mmoles of the same acyl-fluoride and 15 mmoles of isopropylfluoroformate $((CH_3)_2CHOC(O)F)$ and the reaction time is brought to 48 hours. After trap-to-trap distillation 4.35 g of distillate are isolated containing 59% by weight of the desired product with an alkylation yield with respect to the initial acylfluoride of 57%. The selectivity is 82%.

EXAMPLE 5

$CH_3O-CF_2CF_2O(CF_2CF_2O)_m(CF_2O)_nCF_2CF_2-OCH_3$ Synthesis 0.77 g of CsF in powder (5.1 mmoles), 2.10 g of tetraglyme and 4.09 g of diacyl-fluoride $F(O)CCF_2O(CF_2CF_2O)_m-(CF_2O)_nCF_2C(O)F(IA)$ with number average MW (MN) 620, m/n ratio=4.3, functionality of the C(O)F end groups 1.82 (12 mmoles of acyl-fluoride end groups), are introduced by dry-box in a 25 ml autoclave equipped with pressure transducer and magnetic anchor.

After having removed the uncondensable products in a vacuum system ($10^{-3}$ mbar) at −196° C., 20 mmoles of methylfluoroformate are condensed in the autoclave. The autoclave is put in an oil bath maintained at the temperature of 100° C. After 24 hours the heating is interrupted and 2.0 g of methanol are condensed in the autoclave to esterify the unreacted acylfluoride groups. Then the gaseous phase ($CO_2$, HF) is eliminated in a vacuum system and the fluorinated phase is recovered, washed with water. By $^1$H-NMR and $^{19}$F-NMR analyses it results that the reaction yield with respect to the initial acylfluoride is 90%. The selectivity is 100%.

EXAMPLE 6

$CH_3CH_2O-CF_2CF_2O(CF_2CF_2O)_m(CF_2O)_nCF_2CF_2-OCH_2CH_3$ Synthesis 0.38 g of CsF in powder (2.5 mmoles), 2.04 g of tetraglyme and 4.02 g of diacyl-fluoride (IA) of the Example 5 are introduced by dry-box in a 25 ml autoclave equipped with pressure transducer and magnetic anchor. After having removed the uncondensable products in a vacuum system ($10^{-3}$ mbar) at −196° C., 19 mmoles of ethylfluoroformate are condensed in the autoclave. The autoclave is put in an oil bath maintained at the temperature of 100° C. After 48 hours the temperature is increased to 130° C. and it is let react for 24 hours. At the end heating is interrupted and 2.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it results that the alkylation yield with respect to the initial acylfluoride is 96%. The selectivity is 100%.

EXAMPLE 7

$CH_2=CHCH_2O-CF_2CF_2O(CF_2CF_2O)_m(CF_2O)_nCF_2CF_2-OCH_2CH=CH_2$ Synthesis 0.40 g of CsF in powder (2.6 mmoles), 2.03 g of tetraglyme and 4.04 g of diacyl-fluoride (IA) of Example 5 and 2.05 g of allylfluoroformate (19.7 mmoles) are introduced by dry-box in a 25 ml autoclave equipped with pressure transducer and magnetic anchor. After having removed the uncondensable products in a vacuum system ($10^{-3}$ mbar) at −196° C., the autoclave is put in an oil bath maintained at the temperature of 100° C. After 24 hours heating is interrupted and 2.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it results that the alkylation yield with respect to the initial acylfluoride is 90%. The selectivity is 100%.

EXAMPLE 8

$CF_3O-(CF_2CF_2O)_m(CF_2O)_nCF_2CF_2-OCH_3$ Synthesis 0.152 g of CsF in powder (1.0 mmoles), 1.0 g of tetraglyme and 2.36 g of mono-acylfluoride $CF_3O-(CF_2CF_2O)_m-(CF_2O)_nCF_2C(O)F$ (IB) with number average molecular weight (MN) 590, m/n ratio=4.45 and functionality of the C(O)F end groups 1.0 (4.0 mmoles of acyl-fluoride end groups), are introduced by dry-box in a 25 ml autoclave equipped with pressure transducer and magnetic anchor.

After having removed the uncondensable products in a vacuum system ($10^{-3}$ mbar) at $-196°$ C., 8 mmoles of methylfluoroformate are condensed in the autoclave. The autoclave is heated by an oil bath to the temperature of $100°$ C. and maintained at this temperature for 48 hours. The reaction is followed checking the internal pressure. When the reaction is over, 1.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it is found that the alkylation yield with respect to the initial acylfluoride is 97%. The selectivity is 100%.

By following during the reaction the pressure increase in the time, due to the $CO_2$ formation, it has been noticed that the alkylation yield with respect to the initial acylfluoride is higher than 80% already after the first 8 hours, showing that the reaction gives high yields in the desired product also in short times.

EXAMPLE 9

Synthesis

One proceeds as in the Example 8 but by condensing in the autoclave 8 mmoles of ethylfluoroformate. The autoclave is heated by an oil bath to the temperature of $100°$ C. and maintained at this temperature for 48 hours and the reaction is followed by checking the internal pressure. When the reaction is over, 1.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it results that the alkylation yield with respect to the initial acylfluoride is 82%. The selectivity is 100%.

EXAMPLE 10

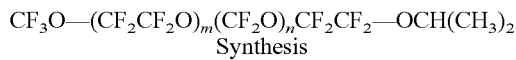
Synthesis

One proceeds as in the Example 8 but by condensing in the autoclave 8 mmoles of isopropylfluoroformate. The autoclave is heated by an oil bath to the temperature of $100°$ C. and maintained at this temperature for 48 hours. The reaction is followed by checking the internal pressure. When the reaction is over, 1.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it results that the alkylation yield with respect to the initial acylfluoride is 90%. The selectivity is 100%.

EXAMPLE 11

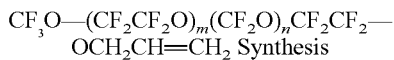
$OCH_2CH=CH_2$ Synthesis

One proceeds as in the Example 8 but by condensing in the autoclave 8 mmoles of allylfluoroformate. The autoclave is heated by an oil bath to the temperature of $100°$ C. and maintained at this temperature for 48 hours. The reaction is followed by checking the internal pressure. When the reaction is over, 1.0 g of methanol are condensed in the autoclave. Then the gaseous phase ($CO_2$, HF) is eliminated by a vacuum system and the fluorinated phase is recovered, washed with water. By $^1$H-NMR and $^{19}$F-NMR analyses it results that the alkylation yield with respect to the initial acylfluoride is 98%. The selectivity is 100%.

By following during the reaction the pressure increase in the time, due to the $CO_2$ formation, it has been noticed that the alkylation yield with respect to the initial acylfluoride is higher than 80% already after the first 8 hours, showing that the reaction gives high yields in the desired product also in short times.

EXAMPLE 12

 Synthesis 0.38 g of CsF in powder (2.5 mmoles) and 1.02 g of tetraglyme are introduced by dry-box in a 25 ml autoclave equipped with pressure transducer and magnetic anchor. After having removed the uncondensable products by a vacuum system, 15.6 mmoles of hexafluoroacetone and 16.7 mmoles of methylfluoroformate are condensed in the autoclave. The autoclave is put in an oil bath maintained at the temperature of $100°$ C. After 36 hours the heating is stopped and the autoclave content is transferred in a vacuum system. By a trap-to-trap distillation with traps maintained, respectively, at the temperatures of $-78°$ C., $-115°$ C. and $-196°$ C., 2.84 g of pure product are isolated in the trap at $-115°$ C., with an alkylation yield with respect to the initial hexafluoroacetone of 91%. The selectivity is 100%.

EXAMPLE 13

 Synthesis 0.36 g of CsF in powder (2.4 mmoles) and 2.01 g of tetraglyme are introduced by dry-box in a 25 ml autoclave equipped with magnetic anchor. After having removed the uncondensable products by a vacuum system, 10 mmoles of acylfluoride ($CF_3O$) ($CF_3$)CFCOF and then 15 mmoles of methylfluoroformate $CH_3OC(O)F$ are condensed in the autoclave. The autoclave is put in an oil bath maintained at the temperature of $100°$ C. After 24 hours the heating is stopped and the autoclave content is transferred in a vacuum system; by a trap-to-trap distillation with traps maintained, respectively, at the temperatures of $-78°$ C., $-110°$ C. and $-196°$ C., 2.88 g of a raw product are isolated in the trap at $-78°$ C.; they analyzed by GC, result to contain 93% by weight of ($CF_3O$) ($CF_3$)$CFCF_2OCH_3$, with an alkylation yield with respect to the initial acylfluoride of 100%.

EXAMPLE 14

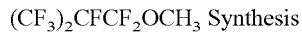 Synthesis

One proceeds as in the Example 1, but by feeding 10.9 mmoles of $(CF_3)_2CFCOF$ and 17 mmoles of methylfluoroformate $CH_3OCOF$. After trap-to-trap distillation, 2.71 g of distillate are isolated containing 72% by weight of the desired product with an alkylation yield with respect to the initial acylfluoride of 71%. The selectivity is 95%.

EXAMPLE 15

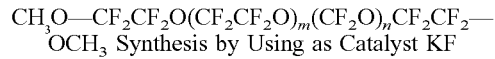
$OCH_3$ Synthesis by Using as Catalyst KF

The Example 5 is repeated but by using as catalyst KF (5.1 mmoles), at the place of CsF and stopping the heating after 48 hours.

The alkylation yield with respect to the initial acylfluoride is 85%. The selectivity is 100%.

The invention claimed is:

1. Process for obtaining hydrofluoroethers of formula (I):

$$A\text{-}(R_f)_{n0}\text{—}CF(R_{f1})\text{—}O\text{—}R_h \quad (I)$$

wherein:
n0 is zero or 1;
$R_f$ is a bivalent radical:
$C_1$–$C_{20}$, linear or branched (per)fluoroalkylene, optionally containing one or more oxygen atoms;
—$CFW'O$—$(R_{f2})$—$CFW$—, wherein W and W', equal or different, are F, $CF_3$; $R_{f2}$ is a (per)fluoropolyoxyalkylene containing one or more of the following units, statistically distributed along the chain, $(C_3F_6O)$; $(CFWO)$ wherein W is as above; $(C_2F_4O)$, $(CF_2(CF_2)_z CF_2)$ wherein z is an integer equal to 1 or 2; $(CH_2CF_2CF_2)$;
$R_{f1}$ is F or a $C_1$–$C_{10}$ linear or branched (per)fluoroalkyl or (per)fluorooxyalkyl radical;
$R_h$ is a $C_1$–$C_{20}$, linear, branched when possible, saturated or unsaturated when possible alkyl, or $C_7$–$C_{20}$ alkylaryl, optionally containing heteroatoms selected from F, O, N, S, P, Cl; and/or functional groups preferably selected from —$SO_2F$, —$CH$=$CH_2$, —$CH_2CH$=$CH_2$ and $NO_2$;
A=F, $(R_{h2}O)$—$CF(R_{f4})$—, —$C(O)F$, wherein
$R_{h2}$, equal to or different from $R_h$, has the $R_h$ meanings;
$R_{f4}$, equal to or different from $R_{f1}$, has the $R_{f1}$ meanings;
wherein a mono- or bifunctional carbonyl compound of formula:

$$B\text{—}R_f\text{—}C(O)R_{f1} \quad (IV)$$

wherein B is F or —$C(O)R_{f4}$, $R_f$, $R_{f1}$, and $R_{f4}$ being as above, is reacted with at least one equivalent of a fluoroformate of formula:

$$R\text{—}OC(O)F \quad (III)$$

wherein R=$R_h$ or $R_{h2}$ as above;
in the presence of an ion fluoride compound (catalyst) and of a dipolar aprotic organic compound, liquid and inert under the reaction conditions.

2. A process according to claim 1, wherein the $(C_3F_6O)$ unit of $R_{f2}$ can be $(CF_2CF(CF_3)O)$ or $(CF(CF_3)CF_2O)$.

3. A process according to claim 1, wherein in formula (I) $R_{f1}$, and $R_{f4}$ of A, independently the one from the other, are F, $CF_3$.

4. A process according to claim 1, wherein when $R_f$ of formula (I) is a (per)fluoroalkylene, $R_f$ is selected from the following groups:
—$CF_2$—, —$CF_2CF_2$—, —$CF_2CF_2CF_2$—, —$CF_2(CF_3)CF$—; when $R_f$ contains one oxygen atom it is —$CF_2(OCF_3)CF$—.

5. A process according to claim 1, wherein $R_{f2}$ is a perfluoropolyoxyalkylene chain having number average molecular weight from 66 to 12,000.

6. A process according to claim 5, wherein when $R_{f2}$ is a perfluorooxyalkylene chain it is selected from the following structures:
a) —$(CF_2CF_2O)_m(CF_2O)_n(CF_2CF(CF_3)O)_p(CF(CF_3)O)_q$—;
b) —$(CF_2O)_n(CF_2CF(CF_3)O)_p(CF(CF_3)O)_q$—;
c) —$(CF_2CF_2O)_m(CF_2O)_n$;
wherein:
m is comprised between 0 and 100 extremes included;
n is comprised between 0 and 50 extremes included;
p is comprised between 0 and 100 extremes included;
q is comprised between 0 and 60 extremes included; and m+n+p+q>0.

7. A process according to claim 6, wherein $R_{f2}$ is a perfluorooxyalkylene c), and the m/n ratio ranges from 0.1 to 10, n being different from zero and the number average molecular weight comprised within the above limits.

8. A process according to claim 1, wherein in formula (I) $R_h$ and $R_{h2}$ having the following meanings:
—$CH_3$, —$CH_2CH_3$,
—$CH_2CH_2CH_3$, —$CH(CH_3)_2$, —$CH_2CH$=$CH_2$.

9. A process according to claim 1, wherein the ion fluoride compound is any compound capable to generate ion fluorides when, in the presence of dipolar aprotic solvents, at temperatures from 20° C. up to 200° C., said dipolar aprotic solvents being acetonitrile, dimethyl-formamide, glyme, ethylene polyoxides dimethylethers (PEO-dimethylethers).

10. A process according to claim 9, wherein the ion fluoride compound is selected from the group consisting of metal fluorides; AgF; alkylammoniumfluorides, alkylphosphonium-fluorides, wherein the nitrogen and respectively the phosphor atom can be substituted with one or more $C_1$–$C_8$ alkyl groups, equal to or different from each other.

11. A process according to claim 9, wherein the ion fluoride compound is CsF and KF.

12. A process according to claim 9, wherein the catalyst is optionally supported.

13. A process according to claim 1, wherein the catalyst amounts, expressed in % moles, are in the range 0.1%–50% with respect to the mono-or bifunctional carbonyl compound of formula (IV).

14. A process according to claim 1, wherein the dipolar aprotic organic compound is selected from the group consisting of acetonitrile, dimethylformamide, glyme, ethylene polyoxides dimethylethers (PEO-dimethylethers).

15. A process according to claim 1, wherein the ratio by weight between the dipolar aprotic organic compound and the ion fluoride compound ranges from 1:100 to 100:1.

16. A process according to claim 1, wherein tertiary amines and/or phase transfer catalysts are used.

17. A process according to claim 1, wherein the reaction temperature in the process is from 60° C. to 200° C.

18. A process according to claim 1, carried out in a discontinuous way.

19. A process according to claim 1, carried out in a continuous way.

20. A process according to claim 1, wherein $R_f$ is a bivalent radical: $C_2$–$C_{12}$, linear or branched (per)fluoroalkylene, optionally containing one or more oxygen atoms.

21. A process according to claim 1, wherein $R_h$ is a $C_1$–$C_{10}$ linear, branched when possible, saturated or unsaturated when possible alkyl, optionally containing heteroatoms selected from F, O, N, S, P, Cl; and/or functional groups preferably selected from —$SO_2F$, —$CH$=$CH_2$, —$CH_2CH$=$CH_2$ and $NO_2$.

22. A process according to claim 5, wherein $R_{f2}$ is a perfluoropolyoxyalkylene chain having number average molecular weight from 100 to 5,000.

23. A process according to claim 22, wherein $R_{f2}$ is a perfluoropolyoxyalkylene chain having number average molecular weight from 300 to 2,000.

24. A process according to claim 10, wherein the metal fluorides are alkaline or alkaline-earth metal fluorides.

25. A process according to claim 14, wherein the dipolar aprotic organic compound is tetraglyme or PEO-dimethylethers having number average molecular weight in the range 134–2,000.

26. A process according to claim 17, wherein the reaction temperature in the process is from 80°C. to 150° C.

* * * * *